United States Patent [19]

Verhoeven et al.

[11] Patent Number: 4,820,850

[45] Date of Patent: Apr. 11, 1989

[54] PROCESS FOR α-C-ALKYLATION OF THE 8-ACYL GROUP ON MEVINOLIN AND ANALOGS THEREOF

[75] Inventors: Thomas R. Verhoeven, Cranford; David Askin, Edison, both of N.J.

[73] Assignee: Merck & Co., Inc., Rahway, N.J.

[21] Appl. No.: 72,066

[22] Filed: Jul. 10, 1987

[51] Int. Cl.$^4$ ............................................. C07D 309/10
[52] U.S. Cl. ..................................... 549/292; 556/419
[58] Field of Search .................. 549/292, 214; 556/419

[56] References Cited

U.S. PATENT DOCUMENTS

| | | | |
|---|---|---|---|
| 4,444,784 | 4/1984 | Hoffman et al. | 549/292 |
| 4,582,915 | 4/1986 | Sletzinger et al. | 549/292 |
| 4,584,389 | 4/1986 | Sletzinger et al. | 549/292 |
| 4,588,820 | 5/1986 | Stokker et al. | 549/214 |

OTHER PUBLICATIONS

Newton et al., "An Excellent Reagent for the, etc." CA92:214927f (1980).

Primary Examiner—Richard L. Raymond
Assistant Examiner—Patricia L. Morris
Attorney, Agent, or Firm—Melvin Winokur; Joseph F. DiPrima

[57] ABSTRACT

A process for alkylating the alpha position of the 8-acyl side chain in mevinolin and analogs thereof is disclosed. The process proceeds with a single charge of base and alkyl halide to give products with a pharmaceutically acceptable purity.

21 Claims, No Drawings

PROCESS FOR α-C-ALKYLATION OF THE 8-ACYL GROUP ON MEVINOLIN AND ANALOGS THEREOF

BACKGROUND OF THE INVENTION

Compounds of structure (I) are known and known to have HMG-CoA reductase inhibitory properties.

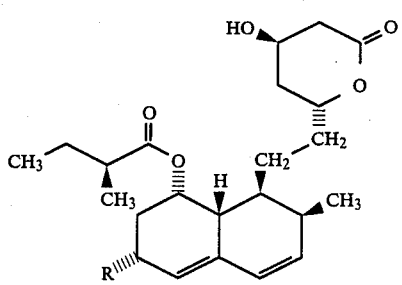

(I)

They are the natural fermentation products mevinolin (R=CH₃, U.S. Pat. No. 4,231,938) and compactin (R=H, U.S. Pat. No. 3,983,140) and derivatives thereof all with the natural 2-methylbutyrate side chain. Compounds of structure (II) with the 2,2 dimethylbutyrate side chain and R=CH₃ are known to be more active inhibitors of HMG-CoA reductase than their 2-methylbutyrate analogs.

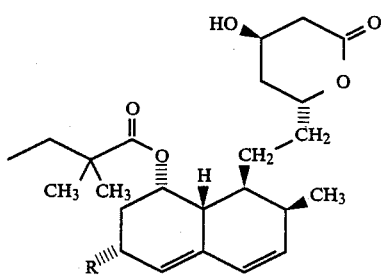

(II)

Some compounds of structure (II) and processes for their preparation are disclosed in U.S. Pat. No. 4,444,784 and EPO published application 33538. However the process disclosed therein involves 4 distinct chemical steps: (1) de-esterification of the 2-methylbutyrate side chain; (2) protection of the 4-hydroxy of the pyranone ring; (3) re-esterification to form the desired 2,2 dimethylbutyrate; and (4) deprotection of the 4-hydroxy group. This route was lengthy and gave low overall yields.

U.S. Pat. No. 4,582,915 ("915") disclosed a novel route to the dimethylbutyrate side chain via direct alkylation of the α-carbon of the naturally available methylbutyrate side chain using a metal alkyl amide and a methyl halide. However this Process has been found to have certain disadvantages in the commercial manufacture of a pharmaceutical. In order to obtain a high conversion of starting material, it was necessary to use a repeat addition of the amide base and methyl halide. This of course exacts a yield penalty and is time-consuming. Furthermore a selective hydrolysis is still necessary to reduce the level of unmethylated starting material to less than 0.7%. This step is time consuming since the hydrolysis of unconverted starting material is very slow and normally requires 20 hours. The overall yield for this process is moderate where the starting material is mevinolin. In addition to unconverted starting material a number of other impurities are generated during the methylation and hydrolysis steps. These include, when the starting material is mevinolin, des-butyratemevinolin and bis-methylated compounds wherein the alpha lactone carbon is methylated in addition to that on the 8'-C-ester side chain, and a methyl ether wherein the ring oxygen of the lactone now in the open form has been methylated. The purity of the final product isolated from the overall process is close to borderline for use as a human health-care product. A process having a less pronounced impurity spectrum would ensure less chance of batch-to-batch variations causing problems in obtaining acceptable final drug purity without resorting to wasteful repeated recrystallizations.

SUMMARY OF THE INVENTION

This invention is a novel process, for alkylating the α-position of an acyl moiety, which may be depicted as:

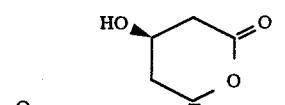
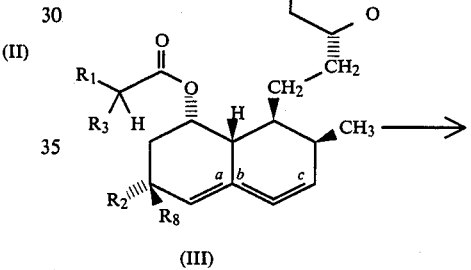

(III)

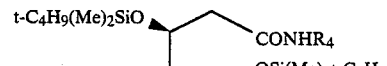
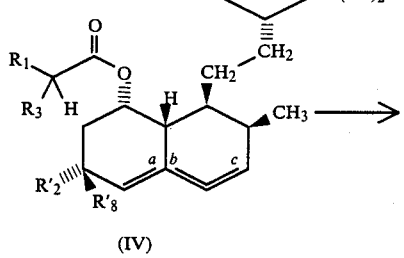

(IV)

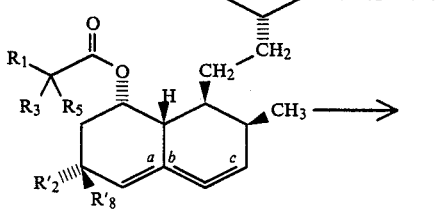

(V)

-continued (VI)

(V)

In particular the process can be used to methylate mevinolin to produce a product which is a more reactive inhibitor of HMG-CoA reductase than mevinolin itself. The reaction proceeds using only a single charge of base and methyl halide to form product in a pharmaceutically acceptable purity.

DETAILED DESCRIPTION OF THE INVENTION

The present invention provides a novel process for alkylating the alpha carbon of the 8'-C-ester side chain of mevinolin and analogs thereof with only a single charge of base and alkyl halide to form a product in substantially higher yield and most importantly at a higher state of purity than a similar product by the "915" route.

The process of the instant invention may be represented by the sequence:

(III)

(IV)

(VI)

wherein
$R_1$ is $C_{1-5}$ alkyl;
$R_2$ is selected from the group consisting of H, $CH_3$, OH or $CH_2OH$;
$R_3$ is H or $C_{1-3}$ alkyl;
$R_4$ is $C_{3-5}$ alkyl;
$R'_2$ is identical to $R_2$ except that where $R_2$ is OH or $CH_2OH$, $R'_2$ is $OSi(Me)_2t\text{-}C_4H_9$ or $CH_2OSi(Me)_2t\text{-}C_4H_9$;
$R_5$ is $C_{1-3}$ alkyl;
$R_6$ and $R_7$ are independently
  (i) $C_{1-3}$ alkyl, or
  (ii) $R_6$ and $R_7$ joined together with the nitrogen to which they are attached form a 5 or 6 membered heterocycle such as pyrrolidine or piperidine;
$R_8$ is selected from the group consisting of H, OH, or $CH_2OH$; Provided that at least one of $R_2$ or $R_8$ is H;
$R'_8$ is identical to $R_8$ except that where $R_8$ is OH or $CH_2OH$, $R'_8$ is $OSi(Me)_2t\text{-}C_4H_9$ or $CH_2OSi(Me)_2tC_4H_9$;
X is chloro, bromo or iodo;
$M^+$ is a cation derived from lithium, sodium or potassium; and a, b and c each represent single bonds or one of a, b and c represents a double bond or both a and c represent double bonds.

Except where specifically defined to the contrary, the term alkyl includes both the straight-chain and branched chain species of the term.

One embodiment of the present invention is the preparation of compounds of structure (V) wherein $R_1$ is ethyl, $R_3$ is methyl and $R_5$ is methyl.

In a class of this embodiment are those compounds wherein $R'_2$ is H, $CH_3$ or $CH_2OSi(Me)_2C_4H_9$. In one subclass are those compounds wherein a and c both represent double bonds. Exemplifying this subclass are the compounds wherein:
$R_1$=ethyl, $R_3$=methyl, $R_4$=n-butyl, $R_5$=methyl and
a. $R'_2$=$CH_3$ and $R'_8$=H; or
b. $R'_2$=$CH_2OSi(Me)_2tC_4H_9$ and $R'_8$=H; or c. R'$_2$=H and R'$_8$=CH$_2$OSi(Me)$_2$tC$_4$H$_9$.

In a second subclass are those compounds wherein a, b, and c are all single bonds. Exemplifying this subclass are the compounds wherein:

R$_1$=ethyl, R$_3$=methyl, R$_4$=n-butyl, R$_5$=methyl, and a. R'$_2$ is CH$_3$ and R'$_8$ is H; or
b. R'$_2$ is CH$_2$OSi(Me)$_2$tC$_4$H$_9$ and R'$_8$ is H; or
c. R'$_2$ is H and R'$_8$ is CH$_2$OSi(Me)$_2$tC$_4$H$_9$.

A second embodiment of the present invention is the preparation of compounds of structure (VI) wherein R$_1$ is ethyl, R$_3$ is methyl and R$_5$ is methyl.

In a class of this embodiment are those compounds wherein R$_2$ is CH$_3$ or CH$_2$OH. In one subclass are those compounds wherein a and c both represent double bonds. Exemplifying this subclass are the compounds:

(1) 6R-[2-[8(S)-(2,2-dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2one;

(2) 6R-[2-[8(S)-(2,2-dimethylbutyryloxy)-2(S)-methyl-6(R)-hydroxymethyl-1,2,6,7,8,8a(R)-hexahydronaphthyl-1(S)]ethyl]-4(R)-hydroxy-3,4,5,6-tetrahydro-2H-pyran-2-one.

In a second subclass are those compounds wherein a, b and c are all single bonds. Exemplifying this subclass are the compounds:

(1) 6(R)-[2-[8(S)-(2,2-dimethylbutyryloxy)-2(S),6(S)-dimethyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(2) 6R-[2-[8(S)-(2,2-dimethylbutyryloxy)-2(S)-methyl-6(R)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one.

The novel process of the instant invention comprises selective C-alkylation at the α-position of the 8'-acyl side chain of the polyhydronaphthyl moiety of structure (III). The C-alkylation occurs in the presence of the β-hydroxy-valerolactone masked as a alkylamide-bis(-tert-butyldimethylsilyl) ether. Good yields are obtained with a single charge of base and alkyl halide. After C-alkylation the alkylamide is cleanly converted to the valerolactone without affecting the C-alkylated acyl side chain. The entire process of protection, C-alkylation and removal of protecting groups is carried out in a single vessel.

The starting lactone is converted into an amide by reaction with an alkylamine, preferably n-butylamine, under an inert atmosphere such as nitrogen. The hydroxyl groups are protected with tert-butyldimethylsilyl chloride or a like reagent, and a base such as imidazole.

The alkali metal amide is formed by combining a hydrocarbon solution of a n-butyl-alkali metal, wherein the alkali metal is lithium, sodium, or potassium, preferably lithium, with a dried solution of R$_6$R$_7$NH wherein R$_6$R$_7$NH is diethylamine, dimethylamine, diisopropylamine or pyrrolidine, preferably pyrollidine in an ethereal solvent such as tetrahydrofuran, diethyl ether, 1,2 dimethoxyethane preferably tetrahydrofuran at a temperature of about −20° C.

The solution of hydroxyl-protected alkyl amide previously formed is cooled to about −35° C., and the solution of alkali metal amide added at such a rate so as to maintain the temperature below −30° C. The solution is aged at about −35° C. for approximately 2 hours. A dried alkyl halide, preferably methyl chloride, methyl bromide or methyl iodide, most preferably methyl iodide, is added to the mixture in one portion.

The mixture is recooled to about −30° C. for approximately 1 hour after the alkyl halide addition, then it is warmed to about −10° C. over a period of about 20 minutes, and aged for approximately 20 minutes at about −10° C. The reaction mixture is quenched with an excess of water, and extracted with a hydrocarbon solvent such as cyclohexane or the like.

The tert-butyldimethylsilyl protecting groups are removed by treatment with an acid such as aqueous hydrofluoric acid. Aqueous sodium hydroxide is added to bring the solution pH to exactly 6.5 while not allowing the temperature to rise above 10° C.

The above solution is charged with 2.0 N NaOH and brought to reflux for 1 to 6 hours, preferably 3 hours. The mixture is cooled to 25° C., diluted with water and the solvent distilled under vacuum. The mixture is cooled to about 10° C. and carefully acidified with 3.0 N HCl to pH 7.0. Ethyl acetate is added and the layers separated. The ethyl acetate layer is washed with water. Methanol is added and the mixture warmed to about 20° C. as aqueous NH$_3$ is added to crystallize out the NH$_4$ salt of the lactone over a period of about 15 minutes. Once crystallization is underway the mixture is warmed to 35° to 50° C. for 5 to 60 minutes preferably 45° C. for 15 minutes and then cooled to +10° to −20° C. for 0.5 to 12 hours, preferably −10° C. for 2.5 hours. The ammonium salt is washed with ethyl acetate/ methanol and dried in vacuo with a nitrogen purge.

The crude ammonium salt is suspended in a hydrocarbon solvent such as toluene and heated at 90° to 110° C. for 2 to 12 hours, preferably 100° C. for 3.5 hours, under a purge of nitrogen. The mixture is cooled to 25° C. filtered and the filtrate concentrated in vacuo maintaining the internal temperature below 40° C. A hydrocarbon solvent such as cyclohexane is added and the mixture heated at reflux for 0.1 to 1 hour, preferably 0.25 hour then cooled for 1 to 12 hours at 25° to 10° C., preferably 2 hours at 10°-15° C. The product lactone is filtered and washed with a cold hydrocarbon solvent such as cyclohexane, then dried in vacuo to give a product of high purity.

The above obtained product is recrystallized from aqueous methanol to yield a product of pharmaceutically acceptable purity as determined by HPLC.

The starting material Lovastatin, wherein R$_1$=ethyl, R$_2$=CH$_3$, R$_3$=CH$_3$ and a and c are double bonds, is readily available or may be prepared according to the fermentation procedures disclosed in U.S. Pat. No. 4,231,938. Hydrogenation derivatives of Lovastatin are prepared following the procedures outlined in U.S. Pat. No. 4,444,784. The starting material compactin wherein R$_1$=ethyl, R$_2$=H and R$_3$=CH$_3$ and a and c are double bonds is prepared according to the fermentation procedure outlined in U.S. Pat. No. 4,231,938. Starting materials wherein R$_2$=CH$_2$OH are prepared following the procedure outlined in copending U.S. Patent application Ser. No. 048136, filed May 15, 1987. Those compounds wherein R$_2$ or R$_8$ is OH are prepared following the procedures in U.S. Pat. Nos. 4,537,859 and 4,517,373.

The following Examples illustrate the present invention and as such are not to be considered as limiting the invention set forth in the claims appended hereto.

EXAMPLE 1

Preparation of 6(R)-[2-[8(S)-(2,2-dimethylbutyryloxy)-2(S),6(R)-dimethyl-1,2,6,7,8,8a(R)-hexahydro-1(S)]ethyl]-4(R)-hydroxy-3, 4, 5, 6-tetrahydro-2H-pyran-2-one (1a) 3,5-bis(tert-butyldimethylsilyl) Lovastatinbutylamide (A compound of formula (IV) wherein $R_1$=ethyl, $R'_2$=methyl, $R_3$=methyl, $R_4$=n-butyl, $R'_8$=H and a and c are double bonds.)

(All manipulations are carried out under a nitrogen atmosphere).

Lovastatin (53.0 g, 0.128 mol) was dissolved in n-butylamine (210 mL, 2.12 mol) at 25° C. and heated to a gentle reflux at 80° C. After 1 hour, the solution was cooled to 25° C., the pressure reduced to 120 mm/Hg and the butylamine distilled at a bath temperature of 60° C. The concentrated solution was cooled to 25° C. and dimethylformamide (263 mL, sieve-dried, K.F. =43) was charged (pot volume =373 mL). The pressure was again reduced to 120 mm/Hg and the mixture heated at 110° C. (bath temperature) for 45 minutes, while collecting 17 mL of distillate. The mixture was then cooled to 25° C. and imidazole (19.59 g, 0.288 mol) and then tert-butyldimethylsilyl chloride (44.4 g, 0.288 mol) were added. The mixture was then heated at 60° C. for 8-14 hours until the silylation had gone to completion. The mixture was cooled to 12° C., and anhydrous methanol (5.8 mL, 0.143 mol) added and the mixture aged at 10°-15° C. for 0.5 hour. The mixture was then partitioned with cyclohexane (1.5 l) and distilled water (750 mL) and vigorously agitated. The layers were separated and the upper (cyclohexane) layer washed with saturated aqueous sodium bicarbonate (750 mL) and distilled water (750 mL).

The cyclohexane layer was distilled at ambient pressure. After 1320 mL of distillate was collected (pot volume =580 mL), the solution was diluted with sieve-dried THF (600 mL) and then 110 mL of distillate was collected while distilling the mixture at ambient pressure. The solution was then cooled to 25° C. for use in the next step.

(1b) 3,5-bis(tert-butyldimethylsilyl)-Synvinolinbutylamide (A compound of formula (V) wherein $R_1$=ethyl, $R'_2$=methyl, $R_3$=methyl, $R_4$=n-butyl, $R'_8$=H and a and c are double bonds.)

A solution of sieve dried pyrrolidine (25.13 mL) and sieve dried THF (192 mL) was cooled to −18° C. A solution of n-butyllithium in hexane (1.65 M, 182.5 mL, 0.301 mol) was added at such a rate as to keep the temperature below −10° C. (approx. 15 minutes). After the addition was complete, the mixture was aged at −20° C. for 15 minutes.

The solution of 3,5-bis(tert-butyldimethylsilyl)Lovastatin butylamide in THF/cyclohexane was cooled to −35° C. The solution of lithium pyrrolidide at −20° C. was then added to the rapidly agitated mixture at such a rate as to maintain the temperature below −30° C. at all times during the addition. The solution was then aged at −35° C. for 2 hours. Sieve dried methyl iodide was added (12.2 mL, 0.196 mol) to the mixture in one portion. The mixture was then recooled to −30° C. and aged for 1 hour after the methyl iodide addition, then it was warmed to −10° C. over a period of 23 minutes and aged for 20 minutes at −10° C.

The mixture was quenched with water (550 mL) and rapidly agitated for 10 minutes. The phases were separated and the lower (aqueous) phase was reextracted with cyclohexane (465 mL). The combined organic phase was washed with 1N HCl (500 mL) and 10% aqueous sodium bisulfite ($NaHSO_3$, 500 mL). The combined organic phase was concentrated at 120 mm/Hg to a volume of 300 mL. This concentrated solution was used directly in the next step.

(1c) Synvinolin-butylamide

The concentrated solution from the previous step was diluted with acetonitrile (600 mL) and the mixture again concentrated at 120 mm/Hg to a volume of 300 mL. The mixture was cooled to 25° C. and acetonitrile (300 mL) was charged. The resulting solution was cooled to +7° C. Hydrofluoric acid (79 mL, 50% aqueous solution) was charged. The mixture was then warmed to 25° C. over a period of 1 hour. The mixture was aged at 25° C. for 1.5 hour, then cooled to +5° C. Aqueous sodium hydroxide (NaOH, 3N) was added carefully to the rapidly agitated mixture to bring the pH of the solution to exactly 6.5. At no time during the caustic addition was the temperature allowed to rise above +10° C. The layers were separated, and the lower (aqueous) phase was back extracted with 788 mL of (THF/cyclohexane) solution (563 mL THF/225 mL cyclohexane). The THF/cyclohexane extract was combined with the initial acetonitrile layer and the combined extracts were concentrated at 120 mm/Hg to a volume of 290 mL. Ethanol (anhydrous, 1000 mL) was charged and the volume was reduced to 788 mL by distillation at 120 mm/Hg. This solution was used directly in the next step.

(1d) Ammonium salt of Synvinolin

To the ethanol solution of Synvinolinbutylamide from the previous step at 25° C. was charged, 2N sodium hydroxide (NaOH, 164 mL) and the resulting solution brought to a gentle reflux (81° C.). After 3 hours the mixture was cooled to 25° C. and diluted with 789 mL of distilled water. The pressure was reduced to 120 mm/Hg and ethanol was distilled. The pot volume was reduced to 788 mL as 840 mL of distillate was collected. The mixture was cooled to +11° C. and carefully acidified with 3.0 N HCl to pH=7.0. Ethyl acetate (925 mL) was added and the aqueous phase further acidified to pH=2.5. The mixture was rapidly agitated for 5-10 minutes and the layers were separated. The lower (aqueous) phase was reextracted with ethyl acetate (463 mL) and combined with the first ethyl acetate layer. The combined ethyl acetate layers were washed with water (360 mL). Methanol (anhydrous, 533 mL) was added and the mixture warmed to +20° C. as 28% aqueous $NH_4OH$ (18.0 mL) was added over a 15 minute period. Once crystallization was underway, the mixture was warmed to 45° C., aged for 15 minutes, then cooled to −10° C. over a 2.5 hour period. After a 1 hour age, the product was filtered and washed with 3:1 ethyl acetate/methanol (338 ml EtOAc/112 mL MeOH, −10° C.). The product was dried in vacuo with a nitrogen purge at 30°-35° C. to give the titled compound of step (1d).

(1e)

6(R)-[2-[8(S)-(2,2-dimethylbutyryloxy)-2(S),6(R)-dimethyl-1,2,6,7,8,8a(R)-hexahydro-1(S)]ethyl]-4(R)-hydroxy-3,4,5,6-tetrahydro-2H-pyran-2-one Lactonization The crude ammonium salt of step (1d) (25.0 g, 52.35 mmole) was suspended in toluene (500 ml) and heated at 100° C. under a constant sweep of nitrogen for 3.5 hours.

The solution was cooled to 25° C. and Darco KB (activated charcoal) (1.25 g) was added. The mixture was agitated at 25° C. for 0.5 hour filtered through SuperCel (diatomaceous earth) and the filtrate concentrated in vacuo to a volume of 50 ml maintaining an internal temperature of <40° C. Cyclohexane (300 ml) was added and the mixture heated at reflux for 0.25 hour then cooled over 2 hours to 10°–15° C. and aged for 1 hour. The product was filtered and washed with cold cyclohexane (115 ml) then dried in vacuo at 30°–35° C. to give the desired compound as a crystalline solid.

Recrystallization

The lactonized product (20.0 g) was dissolved in methanol (240 ml) at 25° C. under $N_2$ then filtered through a pad of Ecosorb-C (homogenous mixture of activated carbon on a fibrous support) (15 g) over 0.25 hour. The Ecosorb-C was rinsed with additional methanol (40 ml). The combined filtrate was heated to 35° C. and water (90 ml) was added over 0.25 hour. The mixture was cooled gradually at a rate of 5° C./0.25 hour until crystallization initiated.

The mixture was aged for 0.5 hour then reheated to 40° C. and the remaining water (190 ml) slowly added over 1 hour. The mixture was cooled to 15° C. over 1.5 hour, aged for 1 hour, filtered and the product washed with methanol:$H_2O$ (1:1 v/v, 90 ml). The product was dried in vacuo at 30°–35° C. with a nitrogen purge to give the titled compound in pharmaceutically acceptable purity as white elongated rods. The titled compound was identified by HPLC.

EXAMPLES 2-4

Following the procedure substantially as described in Example 1 but substituting for the Lovastatin used as starting material therein, approximately equimolar amounts of the compounds of structure (III) as described below there are prepared the 2,2-dimethylbutyrate products as listed below

|  | $R_1$ | $R_2$ | $R_3$ | a | b | c | $R_5$ |
|---|---|---|---|---|---|---|---|
| Example 2 | $CH_3CH_2$ | $CH_3$ | $CH_3$ | — | — | — | $CH_3$ |
| Example 3 | $CH_3CH_2$ | $CH_2OH$ | $CH_3$ | db | — | db | $CH_3$ |
| Example 4 | $CH_3CH_2$ | $CH_2OH$ | $CH_3$ | — | — | — | $CH_3$ |

What is claimed is:

1. A process for the preparation of a compound of structural formula (V):

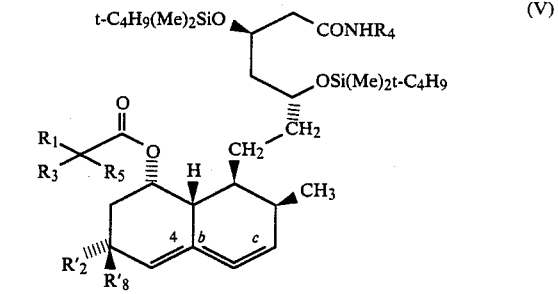

wherein:
$R_1$ is $C_{1-5}$ alkyl;
$R'_2$ is selected from the group consisting of H, $CH_3$, $OSi(Me)_2t\text{-}C_4H_9$ or $CH_2OSi(Me)_2t\text{-}C_4H_9$;
$R_3$ is H or $C_{1-3}$ alkyl;
$R_4$ is $C_{3-5}$ alkyl;
$R_5$ is $C_{1-3}$ alyl; and
$R'_8$ is selected from the group consisting of H or $OSi(Me)_2tC_4H_9$ or $CH_2Si(Me)_2tC_4H_9$; provided that at least one of $R'_2$ or $R'_8$ is H;
a, b and c each represent single bonds or one of a, b, and c represents a double bond or both a and c represent double bonds;

which comprises:
(A) treatment under a inert atmosphere of a compound of structural formula (III):

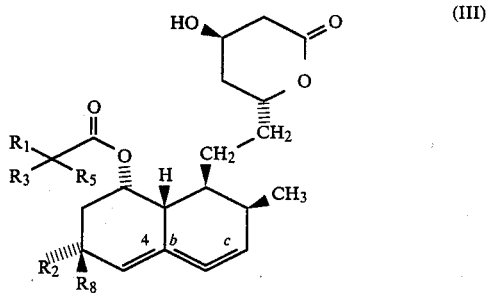

wherein
$R_2$ is selected from the group consisting of H, $CH_3$, —OH, or —$CH_2OH$;
$R_8$ is selected from the group consisting of H or $CH_2OH$; provided that at least one of $R_2$ or $R_8$ is H;
with an alkyl amine $R_4NH_2$, followed by hydroxyl protection with tert-butyldimethylsilyl chloride and imidazole; then
(B) treatment with an alkali metal amide of formula $M^+N^-R_6R_7$;
wherein $M^+$ is a cation derived from sodium potassium or lithium, and
$R_6$ and $R_7$ are independently $C_{1-3}$ alkyl, or $R_6$ and $R_7$ joined together with the nitrogen to which they are attached form a 5 or 6 membered heterocyclic ring; followed by contact with $R_5X$, wherein X is chloro, bromo or iodo.

2. The process of claim 1 wherein Step (B) is conducted in an ethereal solvent, $R_5$ is methyl and the contact with $R_5X$ is at a temperature of $-35°$ to $-10°$ C.

3. The process of claim 2 wherein the ethereal solvent is tetrahydrofuran, the alkyl amine is butylamine and the alkali metal amide is lithium pyrrolidide.

4. The process of claim 3 wherein $R_1$ is ethyl and $R_3$ is methyl.

5. The process of claim 4 wherein $R'_2$ is H, $CH_3$ or $CH_2OSi(Me)_2tC_4H_9$; $R'_8$ is H, or $CH_2OSi(Me)_2tC_4H_9$; provided that at least one of $R'_2$ or $R'_8$ is H.

6. The process of claim 5 wherein a and c both represent double bonds.

7. The process of claim 5 wherein a, b and c all represent single bonds.

8. The process of claim 6 wherein the compound of formula (V) prepared is selected from the group wherein:

a. $R'_2$ is $CH_3$ and $R'_8$ is H; or b. $R'_2$ is $CH_2OSi(Me)_2tC_4H_9$ and $R'_8$ is H; or c. $R'_2$ is H and $R'_8$ is $CH_2OSi(Me)_2tC_4H_9$.

9. The process of claim 7 wherein the compound prepared is selected from the group wherein:

a. $R'_2$ is $CH_3$ and $R'_8$ is H; or b. $R'_2$ is $CH_2OSi(Me)_2tC_4H_9$ and $R'_8$ is H; or c. $R'_2$ is H and $R'_8$ is $CH_2OSi(Me)_2tC_4H_9$.

10. A process of claim 3 further comprising the treatment of a compound of structure (V) with (C) acid in a polar solvent to remove the silyl protecting groups; then (D) treatment with dilute base to hydrolyze the alkyl amide; then (E) heating of the carboxylate salt of the lactone in a hydrocarbon solvent; to form a compound of structure (VI):

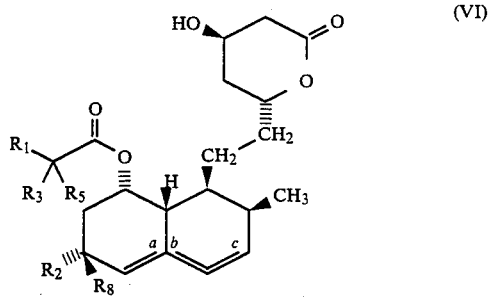

11. The process of claim 10 wherein step (C) the acid is hydrofluoric acid and the polar solvent is acetonitrile.

12. The process of claim 11 wherein step (D) the dilute base is 2.0 N NaOH.

13. The process of claim 12 wherein step (E) the carboxylate salt is heated at 100° C. in toluene.

14. The process of claim 12 further comprising after treatment with NaOH, contact with aqueous ammonia to form the ammonium salt of the lactone.

15. The process of claim 13 wherein the carboxylate salt is the ammonium salt.

16. The process of claim 15 wherein $R_1$ is ethyl and $R_3$ is methyl.

17. The process of claim 16 wherein $R'_2$ is $CH_3$ or $OSi(Me)_2tC_4H_9$ or $CH_2OSi(Me)_2tC_4H_9$.

18. The process of claim 17 wherein a and c both represent double bonds.

19. The process of claim 17 wherein a, b and c all represent single bonds.

20. The process of claim 18 wherein the compound prepared is selected from the group consisting of:
(a) 6(R)-[2-[8(S)-(2,2-dimethylbutyryloxy)-2(S),6(R)-dimethyl-1,2,6,7,8,8a(R)-hexahydronaphthyl-(S)]ethyl]-4(R)-hydroxy-3,4,5,6-tetrahydro-2H-pyran-2-one;
(b) 6(R)-[2-[8(S)-(2,2-dimethylbutyryloxy)-2(S)-methyl-6(R)-hydroxymethyl-1,2,6,7,8,8a(R)-hexahydronaphthyl-1(S)]ethyl]-4(R)-hydroxy-3,4,5,6-tetrahydro-2H-pyran-2-one.

21. The process of claim 19 wherein the compound prepared is selected from the group consisting of:
(a) 6(R)-[2-[8(S)-(2,2-dimethylbutyryloxy)-2(S),6(S)-dimethyl-1,2,3,4,4a,(S),5,6,7,8,8a(S),decahydronaphthYl-1(S)]ethyl]-4(R)-hydroxy-3,4,5,6-tetrahydro-2H-pyran-2-one;
(b) 6(R)-[2-[8(S)-(2,2-dimethylbutyryloxy)-2(S)-methyl-6(R)-hydroxymethyl-1,2,3,4,4a(S),5,6,7,8a(S)-decahydronaphthyl-1(S)]ethyl]-4(R)-hydroxy-3,4,5,6-tetrahydro-2H-pyran-2-one.

* * * * *

UNITED STATES PATENT AND TRADEMARK OFFICE
CERTIFICATE OF CORRECTION

PATENT NO. : 4,820,850
DATED : April 11, 1989
INVENTOR(S) : T. R. Verhoeven, D. Askin It is certified that error appears in the above-identified patent and that said Letters Patent is hereby corrected as shown below:

At Claim 1, column 10, line 10, the 4a,5 double bond labeled "4" should be labeled --a--.

At Claim 1, column 10, line 21, after "$R_5$ is $C_{1-3}$" delete "alyl" and insert therefor --alkyl--.

At Claim 1, column 10, line 42, the 4a,5 double bond labeled "4" should be labeled --a--.

At Claim 20, column 12, line 37, after "hexahydronaphthyl-" delete "(S)" and insert therefor --1(S)--.

At Claim 21, column 12, line 51, after "1,2,3,4,4a(S),5,6,7," insert -- 8 --.

Signed and Sealed this

Seventh Day of November, 1989

*Attest:*

JEFFREY M. SAMUELS

*Attesting Officer*     *Acting Commissioner of Patents and Trademarks*